United States Patent [19]
Nakanishi

[11] 3,994,965
[45] Nov. 30, 1976

[54] D-N-(GUANYLUREIDOACETYL)-α-AMINOPHENYL ACETIC ACID AND D-N-(GUANYLUREIDOACETYL)-α-AMINOPHENYL ACETYL CHLORIDE

[75] Inventor: Susumu Nakanishi, East Lyme, Conn.

[73] Assignee: Pfizer Inc., New York, N.Y.

[22] Filed: Aug. 9, 1974

[21] Appl. No.: 496,200

[52] U.S. Cl. ................... 260/518 R; 260/239.1; 260/544 C
[51] Int. Cl.² ................ C07C 101/02; C07C 63/10
[58] Field of Search ........ 260/518 R, 544 M, 544 C

[56] References Cited
OTHER PUBLICATIONS
Finar, I. L., Organic Chemistry, vol. I (1963), pub. by Richard Clay & Co., pp. 198 & 199, relied on.
Rodd, "Chemistry of Carbon Compounds," vol. I, Part B. (1952), Elsevier Publishing Co., New York, p. 912.
Wagner et al., "Synthetic Organic Chemistry," (1963), J. Wiley & Sons, Inc., New York, p. 646.
Davis et al., "The Jour. of the American Chemical Society," June 1929, vol. 51, No. 6, pp. 1790–1801.
Biilmann et al., "Berichte" (1930), vol. 63, pp. 2205–2208.

Primary Examiner—Anton H. Sutto
Attorney, Agent, or Firm—Connolly and Hutz

[57] ABSTRACT

Method of producing N-(guanylureidoacetyl)-α-aminophenylacetic acid and the utility thereof in the production of N-(guanylureidoacetyl)-α-aminophenylacetyl chloride and the utility of the latter compound for producing the title penicillanic acid.

3 Claims, No Drawings

D-N-(GUANYLUREIDOACETYL)-α-AMINOPHENYL ACETIC ACID AND D-N-(GUANYLUREIDOACETYL)-α-AMINOPHENYL ACETYL CHLORIDE

It is known that 6-[2-phenyl-2-(guanylureidoacetamido)acetamido]penicillanic acid is a broad spectrum antibiotic which, unlike many penicillin analogs, is highly antagonistic toward gram negative microorganisms, in particular, E. coli, Pseudomonas or Klebsiella. See, for example, the disclosure of allowed U.S. Patent application Ser. No. 253,856 as filed May 16, 1972, now U.S. Pat. No. 3,838,153 and incorporated herein by reference.

The present invention is directed to a novel method for producing intermediates for the production of said penicillanic acid in a less complicated and more economical reaction which affords higher yields of higher purity product.

One aspect of the novel process of the present invention is the reaction of a compound of the formula

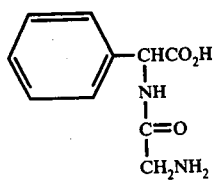

with a compound of the formula

in water at a pH of from 6–7 and a temperature of 80°–100° C., preferably 95°–98° C., to form a compound of the formula

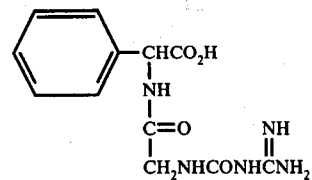

Said reaction is illustrated by I + II → V of the reaction equations presented hereinafter. The N-acetamido-α-aminophenylacetic acid is a readily available material which may be prepared, for example, by the method described in French Pat. No. 684,660. N-guanyl-N'-nitrourea is also readily prepared by, for example, the method described in U.S. Pat. No. 3,579,501.

An alternative method of the present invention for producing compound V is to react α-phenylglycine (III) with guanylureidoacetyl chloride (IV) in a reaction inert solvent at a temperature of 0°–25° C., preferably 10°–15° C. Preferred solvents include dimethylformamide, dimethylacetamide, tetrahydrofuran, dioxane and water, water being especially preferred. The necessary guanylureidoacetyl chloride (IV) or the hydrochloride thereof can be produced by treatment of guanylureidoacetic acid with phosphorous pentachloride in accordance with Example IIB presented hereinafter, the guanylureidoacetic acid being obtainable from N-guanyl-N'-nitrourea and glycine in accordance with the method of Example IIA presented hereinafter.

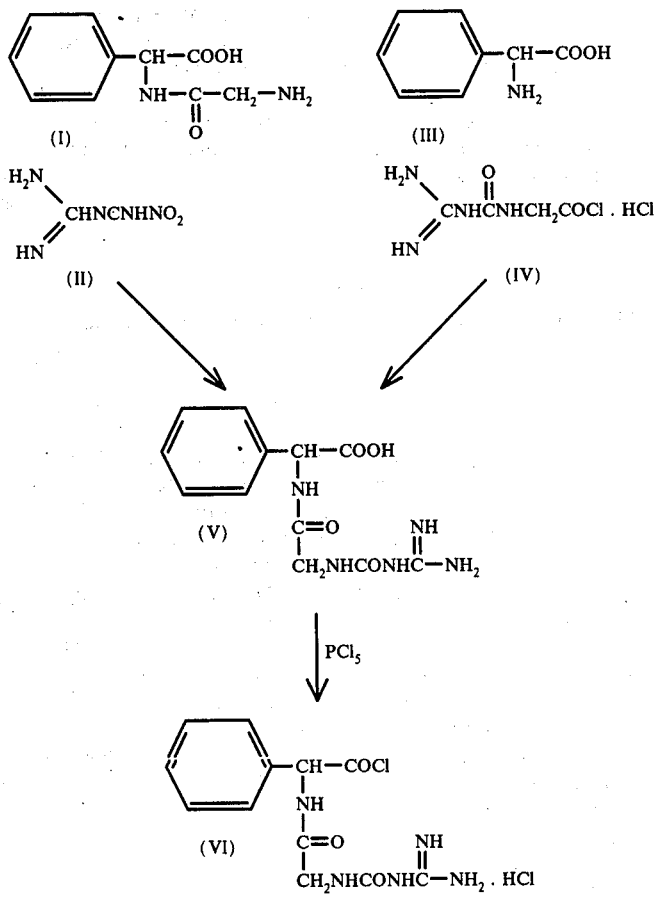

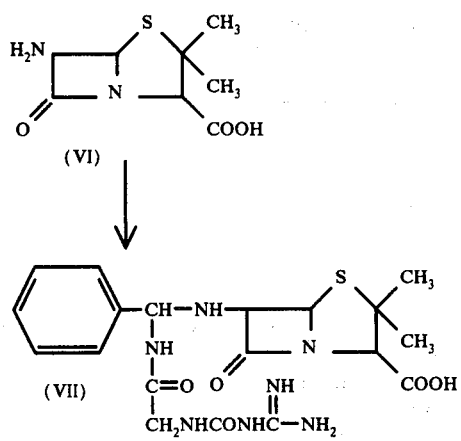

N-guanylureidoacetyl-α-aminophenylacetic acid (V) may be converted to its closely related analog N-(guanylureidoacetyl)-α-aminophenylacetyl chloride (VI) by treatment with phosphorous pentachloride in accordance with Example IIIA presented hereinafter and the resulting compound (VI) may be reacted with 6-aminopenicillanic acid (VII) in accordance with Example IIIB presented hereinafter to obtain the desired 6-[2-phenyl-2-(guanylureidoacetamido)acetamido]-penicillanic acid (VIII).

The aforesaid penicillanic acid (VIII) is preferably of the D-configuration. This is obtained by utilizing D-α-phenylglycine (III) or D-N-acetamido-α-aminophenylacetic acid (I) in the production of intermediate V to obtain the D-configuration for said intermediate, as well as intermediate VI and final product VIII. However, the penicillanic acid (VIII) of the DL-configuration may be prepared by utilizing DL-α-phenylglycine (III) and DL-N-acetylamido-α-aminophenylacetic acid (I).

The following examples are for the purpose of illustrating the preparation and use of the novel intermediates of the present invention.

EXAMPLE I

D-N-(Guanylureidoacetyl)-α-aminophenylacetic Acid (Method I)

The pH of a mixture of 1.0 g. (5 m moles) D(-)-glycyl-2-phenylglycine (French Pat. No. 684,660) and 1.47 g. (10 m moles) of N-guanyl-N'-nitrourea (U.S. Pat. No. 3,579,501) in 20 ml. of water is adjusted to 6.0. The mixture is then heated at reflux temperature for 2 hours, the pH being maintained between 6 and 7 by the addition of 1% aqueous hydrochloric acid. The reaction is then cooled to 10° C., the pH adjusted to 8.5 by the addition of a 2% aqueous sodium hydroxide solution and stirring continued for several minutes. The pH is readjusted to 6.9 (1% aqueous hydrochloric acid) and the resulting precipitate filtered, washed with water and air dried at room temperature, 980 mg., m.p. 221-222° C. (dec.). Karl-Fischer: 1.42% water. Anal. Calcd. for $C_{12}H_{15}O_4N_5$ 1.42%$H_2O$: C, 48.4; H, 5.2; N, 23.5. Found: C, 48.2; H, 5.1; N, 22.7.

EXAMPLE II

D-N-(Guanylureidoacetyl)-α-aminophenylacetic Acid (Method II)

A. Guanylureidoacetic Acid

The pH of a mixture of 29.4 g (0.2 mole) of N-guanyl-N'-nitrourea and 7.5 g. (0.1 mole) of glycine in 200 ml. of water is adjusted to 6.0 and the resulting solution heated to reflux. During the 2 hrs. of reflux (95°–97° C.) the pH of the reaction is maintained between 6 and 7 by the addition of 10% hydrochloric acid. The reaction, after 2 hours reflux, is cooled to 10° C. and the pH adjusted to 6.9. The precipitate is filtered, washed with 500 ml. of water and dried to give 14 g. of the desired intermediate, m.p. 202° C. (dec.).

B. Guanylureidoacetyl chloride Hydrochloride

To 1 gal. of methylene chloride under a nitrogen atmosphere is added 229.06 g. (1.1 moles) of phosphorous pentachloride, and the resulting solution cooled to 10° C. While maintaining the temperature at 10° C., 160.13 g. (1 mole) of guanylureidoacetic acid is added portionwise, and the resulting reaction mixture allowed to stir at room temperature overnight. The product is filtered, washed with dry methylene chloride and used immediately in subsequent reactions without further purification.

C. D-N-(Guanylureidoacetyl)-α-aminophenylacetic Acid

Under a nitrogen atmosphere, 15.1 g. (0.1 mole) of D-α-phenylglycine in 300 ml. of water cooled to 10°–15° C. is treated with 21.2 g. of triethylamine and the suspension allowed to stir for 20 min. at which time a clear solution results. To the resulting solution is added portionwise over a 20 min. period, 23.7 g. (0.11 mole) of guanylureidoacetyl chloride hydrochloride maintaining the temperature at 10°–15° C. After stirring at 10°–15° C. for one hour, the slurry is cooled to 0°–5° C. and the product filtered, washed with cold water and air dried overnight to yield 26 g. of the desired intermediate, m.p. 212°–213° C. (dec.).

The above crude product is suspended in 400 ml. of water, and the pH adjusted to 8.5 by the addition of 2% aqueous sodium hydroxide. After the solution has stirred at room temperature for 10 minutes, the pH is adjusted to 6.98–7.0 with 1% hydrochloric acid and the resulting slurry allowed to stir for 5 minutes. The solids are filtered, washed with 150 ml. of water and air dried to give 20 g of pure product, m.p. 221°–222° C. (dec.). Anal. Calcd. for $C_{12}H_{15}O_4N_5$.2.95% $H_2O$: C, 47.6; H, 5.3; N, 23.1. Found: C, 47.5; H, 5.0; N, 23.8. By infrared and nuclear magnetic resonance spectroscopy, the product is identical with that prepared by Method I.

EXAMPLE III

6-[D-2-Phenyl-2-(guanylureidoacetamido)acetamido]penicillanic Acid

A. D-N-(Guanylureidoacetyl)-α-aminophenylacetyl chloride hydrochloride

To a solution of 12 g. (58 m moles) of phosphorous pentachloride in 110 ml. of dry methylene chloride and maintained to 10°–20° C. is added portionwise over a period of 15 min. 10 g. (29 m moles) of D-N-(guanylureidoacetyl)-α-aminophenylacetic acid. The reaction mixture, after stirring at room temperature for 18 hours, is filtered, and the crystalline acid chloride hydrochloride dried in vacuo, 10.3 g. $[\alpha]_D^{25} = 16.3$ (C = 1, 1% of 5N hydrochloric acid/water).

B. 6-[D-2-Phenyl-2-(guanylureidoacetamido)acetamido]penicillanic acid

Triethylamine (4.46 g., 44 m moles) is added to a cooled (5° C.) mixture of 4.54 g. (21 m moles) of 6-aminopenicillanic acid in 50 ml. of dimethylacetamide under a nitrogen atmosphere, and the mixture allowed to stir at −5° to 0° C. for 15 min. Over a 5 min. period, 10.3 g. (23 m moles) of D-N-(guanylureidoacetyl)-α-aminophenylacetyl chloride hydrochloride is added at such a rate that the temperature does not rise above 0° C. The mixture is stirred at 0° C. for 1 hour, and is subsequently allowed to warm to room temperature. The triethylamine hydrochloride is filtered and the filtrate added dropwise to 600 ml. of chloroform. The precipitated product is filtered, washed with acetone and then triturated in 300 ml. of acetone for 30 min. The desired product is filtered, and dried in vacuo at room temperature until a constant weight is reached, 2.65 g. The product is identical with that prepared by known procedures (Belgium Pat. No. 798,170).

What is claimed is:
1. A compound selected from the group consisting of those of the D-configuration having the formula

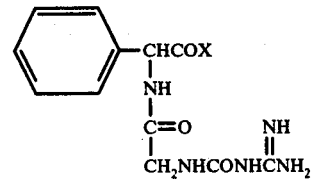

and the hydrochloride addition salt thereof, wherein X is selected from the group consisting of OH and Cl.
2. A compound of claim 1 wherein X is OH.
3. A compound of claim 1 wherein X is Cl.

* * * * *